United States Patent [19]

Haverkamp et al.

[11] Patent Number: 6,010,611
[45] Date of Patent: Jan. 4, 2000

[54] MEASUREMENT OF ALUMINA IN REDUCTION POTS

[75] Inventors: Richard Gerard Haverkamp, Titirangi; Barry John Welch, Orakei, both of New Zealand

[73] Assignee: Auckland Uniservices Limited, Auckland, New Zealand

[21] Appl. No.: 09/029,653

[22] PCT Filed: Aug. 28, 1996

[86] PCT No.: PCT/NZ96/00088

§ 371 Date: Apr. 14, 1998

§ 102(e) Date: Apr. 14, 1998

[87] PCT Pub. No.: WO97/09468

PCT Pub. Date: Mar. 13, 1997

[30] Foreign Application Priority Data

Sep. 1, 1995 [NZ] New Zealand ............................ 272913

[51] Int. Cl.[7] ................................ C25C 3/06; C25C 3/20
[52] U.S. Cl. ...................... 205/336; 205/775; 204/243.1; 204/294
[58] Field of Search .................... 205/336, 775; 204/243.1, 294

[56] References Cited

U.S. PATENT DOCUMENTS

| | | | |
|---|---|---|---|
| 3,471,390 | 10/1969 | Kibby et al. ...................... | 205/336 X |
| 4,126,525 | 11/1978 | Wakaizumi et al. ................ | 205/336 |
| 4,488,117 | 12/1984 | Seo ..................................... | 205/775 |
| 4,639,304 | 1/1987 | Bader et al. ........................ | 205/336 X |
| 4,764,257 | 8/1988 | Sadoway ............................ | 205/336 |
| 4,814,050 | 3/1989 | McGraw et al. . | |

FOREIGN PATENT DOCUMENTS

| | | |
|---|---|---|
| 5750890A1 | 12/1991 | Australia . |
| 58035274 | 12/1975 | Japan . |
| 58035275 | 12/1975 | Japan . |
| 52-1063089 | 3/1976 | Japan . |
| 55-145188 | 5/1979 | Japan . |
| 58061289 | 10/1981 | Japan . |
| 1423627A1 | 10/1986 | U.S.S.R. . |
| 1768664A1 | 5/1990 | U.S.S.R. . |
| 1724713A1 | 8/1990 | U.S.S.R. . |
| 8605008A1 | 8/1986 | WIPO . |

OTHER PUBLICATIONS

"An Improved Algorithm for Identifying Objects in Code", G. Canfora, A. Cimitile, and M. Munro, Software–Practice and Experience. vol. 26(1), 25–48 (Jan. 1996).

"An Object Finder for Program Structure Understanding in Software Maintenance", Roger M. Ogando, Stephen S. Yau, Sying S. Liu, and Norman Wilde, Software Maintenance: Research and Practice. vol.6. 261–283 (1994). (N. month).

"Object–Orientated Re–Architecturing", Harald Gall, Rene Klosch, and Roland Mittermeir, in: 5th European Software Engineering Conference (ESEC '95), Lecture Notes in Computer Science, Sep. 1995.

*Primary Examiner*—Donald R. Valentine
*Attorney, Agent, or Firm*—Watson Cole Grindle Watson P.L.L.C.

[57] ABSTRACT

This invention provides apparatus and a method for measuring the concentration of alumina in a molten electrolyte in a smelter. A test anode (101) (a mimic of the actual cell anode) supplied from a computer-controlled voltage source (303) with several to about (100) rapid cyclic voltammetry sweeps the voltage at which the anode effect occurs, as sensed by current measurement (305). In order to derive a measurement the voltage is compared within the computer (301) to previous measurements made from a calibration set of alumina samples in known concentrations. Brief rapid cycles and an improved electrode configuration help to provide results from the invention which are reproducible and accurate, and in addition the test electrode has a long life.

11 Claims, 5 Drawing Sheets

MEASUREMENT OF ALUMINA IN REDUCTION POTS

FIELD

This invention relates to a method and an apparatus for selective electrochemical measurement of components of an electrolyte. It relates to measuring the concentration of oxide ions (ore) dissolved in a bath (a reduction cell or pot) based on molten halides. In particular it relates to the measurement of the concentration of dissolved aluminium oxide in smelter pots (where the electrolyte consists partly of wholly of fluoride salts) for the production of aluminium.

BACKGROUND

In industrial aluminium reduction cells or pots, where aluminium oxide is dissolved in a bath based on molten halides, one of the main concerns of the operator and also the main difficulty is to monitor the proportion of oxide ions (dissolved alumina) in the electrolyte. An excess of oxide which is soluble to about 7–8% results in the formation of sludge in the bottom of the crucible with highly prejudicial consequences in regard to progress of the electrolysis operation, while impoverishment of oxide ions results in a polarisation action, referred to as an "anode effect" which interferes with the operation of the cells. The anode effect is well known in aluminium smelters. It is related to current density or, in effect, applied voltage and causes the cell resistance to exhibit a sudden large increase above a critical current density Direct and indirect methods and apparatus for determining the amount of dissolved oxide ions have been proposed. Indirect methods include those disclosed in U.S. Pat. No. 4,814,050 (Alcoa) and U.S. Pat. No. 5,025,219 (Pechiney). Direct methods are disclosed in U.S. Pat. No. 3,471,390 (Reynolds; inventors Kibby et al), U.S. Pat. No. 345,063 (Reynolds) and U.S. Pat. No. 4,935,107 (Pechiney). U.S. Pat. No. 3,471,390 discloses apparatus including a probe or test electrode having a cathodic graphite tip, a boron nitride spacer, and an anode, serving as a miniature reduction cell within which a rising voltage will elicit a rising current until such time as the "anode effect" appears, causing a rise in resistance and hence a drop of current. This effect depends primarily on the concentration of alumina in the electrolyte. Kibby's electrode is a plane surface on the end of a rod, having a graphite centre surrounded by an insulating ring. Kibby et al prefer to apply voltage changes in discrete steps over a predetermined period of time, and data is taken from the instrumentation by reading the dials of voltage and current meters. However, the extended duration of a single reading tends to result in significant electrode consumption and therefore the calibration drifts with time. The direct methods disclosed in the other patents referred to above also lack reproducibility and are therefore are not widely used.

STATEMENT OF INVENTION

In a first broad aspect the invention provides a method for measuring the concentration of alumina in a molten electrolyte in a bath, using the characteristic "anode effect" produced by an electrode assembly means having a cathode and an anode and which assembly means is placed in the bath, wherein at least one rapid cyclic voltammetry sweep is applied to the electrode assembly means by means of a voltage-controlled source of electric power connected to the electrode assembly, and the current passing through the electrode assembly means is monitored during the or each sweep in order to detect the anode effect, and the voltage at which the anode effect is observed is recorded, in order to derive information capable of providing a measurement.

In a related aspect the invention provides that the or each rapid cyclic voltammetry sweep comprises a substantially linear change in voltage and is applied to the anode of the electrode assembly means at a rate of voltage change of between +5 to +100 volts per second during a first measurement phase, to reach a potential which is more than sufficient to produce an anode effect, and then is returned at a rate of between −50 to −1000 volts per second during a second, return phase prior to a rest phase.

In a further related aspect the invention provides that the constant rate of voltage change during the first measurement phase is between +20 V.s−1 and +50 V.s−1, and the constant rate of voltage change during the second return phase is typically between −100 V.s−1 and −300 V.s−1.

In another related aspect the invention provides a method for measuring the concentration of alumina in a smelting pot as described previously, in which a small offset potential difference is applied between the working electrode and the counter electrode so that the working electrode is maintained in an anodic state and the counter electrode is maintained in a cathodic state between voltammetry sweeps.

Preferably the offset potential is under one volt, and more preferably it is about 0.3 volts. Alternatively it may be a current source of less than 100 mA, preferably about 60 mA.

In yet another related aspect the invention provides a method for measuring the concentration of alumina in a smelting pot as described previously, wherein prior to measurement the working electrode is conditioned by carrying out between 1 and 200 cyclic linear voltammetry sweeps.

In a yet further related aspect the invention provides a method for measuring the concentration of alumina in a smelting pot as described above, wherein after placement and prior to measurement a predetermined low voltage is applied between the working electrode and the counter electrode and the current flow resulting from this voltage is monitored in order to detect an increase of current indicating that the frozen material about the electrode has been melted.

In a yet further related aspect the invention provides a method for measuring the concentration of alumina in a smelting pot as described previously, wherein the proportion of oxide ions is calculated using at least some of the following information: the potential at which the anode effect occurs, the potential at which the peak current is observed, the magnitude of the peak current, the area of the entire voltammogramme—and then calculating the proportion of oxide ions with reference to a calibration curve.

In an additional related aspect the invention provides a method for measuring the concentration of alumina in a smelting pot as previously described, wherein the proportion of oxide ions is calculated using at least some of the following information: the potential at which the peak current is observed, the potential at which the peak current has reverted to about half its peak value—and then calculating the proportion of oxide ions with reference to a calibration curve.

In another broad aspect the invention provides apparatus suitable for measuring the concentration of alumina in a smelting pot according to the method as described above wherein the electrode assembly means of the apparatus includes an exposed carbon anode having an elongated shape with a length to width ratio of more than about 2.0, and a cathode.

In a related aspect the invention provides apparatus suitable for measuring the concentration of alumina in a smelting pot according to the method as described above wherein the apparatus includes automated means capable of applying a varying yet controlled voltage across the electrode assembly, the means being capable of causing the controlled voltage to rise from a first value to a second value at a first controlled rate, and then to return from the second value to the first value at a second controlled rate, the apparatus also including means capable of recording, at any applied voltage, the current passing between the working electrode and the counter electrode, and means capable of extracting at least the anode effect voltage from the recorded current information.

In a further broad aspect the invention comprises apparatus for measurement of a component of a molten electrolyte in a container, wherein the container comprises an electrolysis cell or "pot" for the production of a metal.

Preferably the component is aluminium oxide, dissolved in a suitable flux, such as a fluoride.

A preferred counter-electrode or cathode geometry comprises a radial assembly of fins made of "Inconel", comprising the counter electrode, surrounding an exposed tip of graphite, comprising the working electrode.

OBJECT

It is an object of this invention to provide an improved method for measuring the concentration of an electrolyte in a bath, or at least to provide the public with a useful choice.

DRAWINGS

It should be noted that the preferred embodiments which are to be described and illustrated herein are simply an example of the invention in its general sense, and are not to be read as in any way limiting as to the scope of the invention. The results presented here are based on laboratory trials.

DESCRIPTION OF THE INVENTION

The measurement process which forms the basis of the invention is termed by us as "modified linear sweep cyclic voltammetry" which, like that of Kibby et al (U.S. Pat. No. 3,471,390) relies on detection of the "anode effect". This process involves fast sweeps of voltage from a resting value up to perhaps 6–7 volts, which is over the threshold of the anode effect. It has the advantage over chronopotentiometry (or chronoamperometry) in that the maximum voltage, and the duration of the maximum voltage, applied to the electrode is much less so that the electrode suffers much less wear and consequently has a longer and more reliable life.

In our laboratory version at least, about 150 sweeps or voltammogrammes are required to condition a new electrode, meaning to bring it to a stable sensitive state, and the conditioned electrode is then good for 2000–4000 voltammogrammes. The results are also more reproducible and more accurate.

Other features of this method include the absence of the need for a reference electrode as would normally be used in voltammetry. In this invention the working electrode serves the function that would normally be carried out by the reference electrode.

For carrying out the modified linear sweep voltammetry and the control strategy two electrodes are first placed in a molten bath, namely the working electrode and the counter electrode. The working electrode is made from carbon. For example the preferred anode material, graphite, is Union Carbide CMG grade or the like. It may be made of glassy carbon.

The counter electrode, which is preferably of a large surface area with respect to the working electrode, may be made from any conducting material that is able to withstand short periods immersed in the molten halide electrolyte mixture, for example it may be the nickel-chromium-iron alloy "Inconel", or steel (which will be more corrosion-prone, but in any case the electrode has a limited life) or copper, which transfers heat well, but is close to its melting point, or for example graphite.

Because there is a tendency for electrolyte to seep between the anode and its surrounding insulation and there degrade the sharpness of the voltammetry curve, we prefer to "swamp" this effect by using a protruding and relatively thin anode, so that there is a significant surface area relative to the inevitable seeping electrolyte. Also, a thin anode has a smaller circumference. Of course, too thin an anode will be eaten away too soon. Practically, a cylinder length:width ratio of at least 2:1 is a suitable anode shape—describing that portion that extends beyond the insulation.

The electrodes may preferably be formed into one unit where the counter electrode forms a cylinder with fins radiating out from it to form an increased surface area for heat transfer, so that the assembly reaches an operating temperature (of the order of 1000° C.) more quickly, and to satisfy the electrochemical requirement of a large surface. The working electrode is concentric to the counter electrode and is composed of graphite. The working electrode is separated from the counter electrode by an electrical insulator such as boron nitride. The lower part of the counter electrode may have holes in it or cutaway sections to allow circulation of electrolyte to the working electrode while at the same time providing physical protection for the working electrode.

Figure 1:
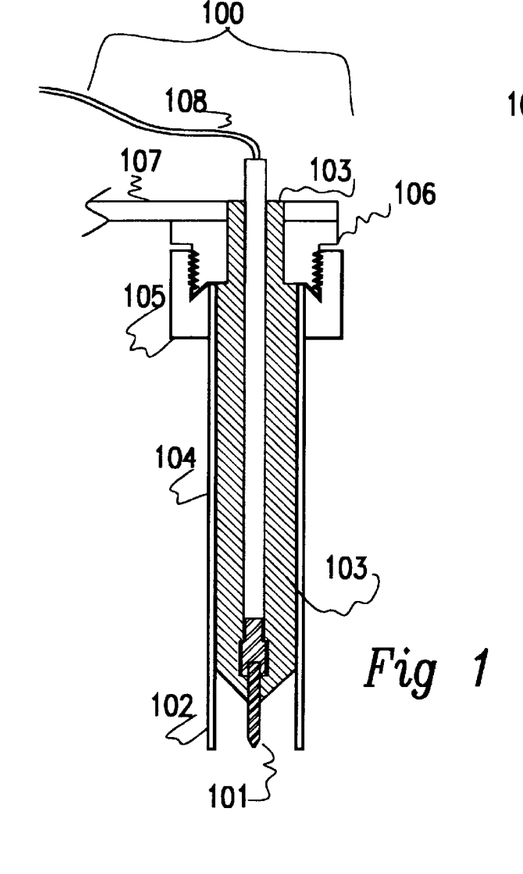
FIG. 1. Section of a preferred example of a probe, made of graphite, boron nitride, "Inconel" and stainless steel.
Figure 2:
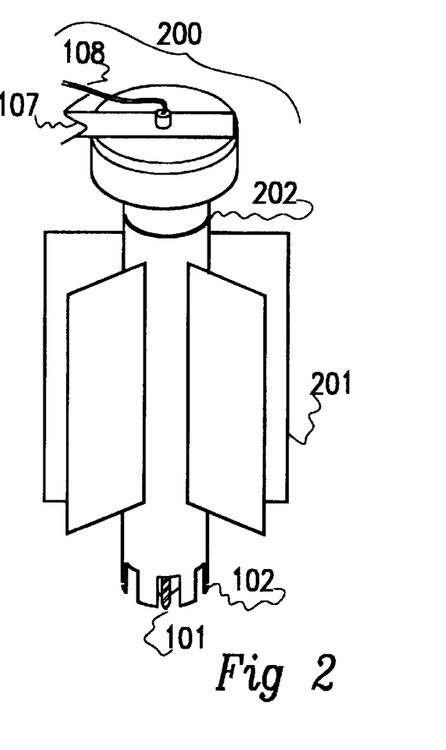
FIG. 2. External appearance of a preferred example of the probe of FIG. 1.

An example of such an electrode is shown schematically and in section as 100, in FIG. 1. Here, the working electrode 101 projects from the base of the assembly. It is surrounded by a sheath of insulation 103 (preferably boron nitride) which in turn is surrounded by a cylinder 104 of "Inconel" or the like, that forms both the counter electrode (or cathode) and a protective sheath about the working electrode. The working electrode may be replaced from time to time. In order to facilitate replacement, the upper end of the electrode assembly (105, 106) screws together and the lower portion 105 is swaged on to the outer cylinder 103. A horizontally produced "handle" connected to the counter electrode serves as a support, and a wire 108 coupled to the working electrode comprises the second electrical connection. Since preparing this prototype we have come to prefer that the electrode is instead supported by a pipe swaged onto the end of the electrode, and bent in such a way as to provide easiest access into a given design of pot. FIG. 2 shows the electrode assembly 200 from the exterior, and here a number of fins of metal 201 are shown, and a castellated lower end to the "Inconel" tube 104 provides better access of the electrolyte to the working electrode.

Our instrumentation (see FIG. 3) provides for automated cyclic linear voltammetry, with automatic cycle generation at a constant rate (preferably rising at between 5 and 100 $V.s^{-1}$ (volts per second) then falling preferably about ten times faster) and means for deriving readings from a statistically significant number of cycles. Our instrumentation includes computer facilities for locating the position of the anode effect and relating it to stored calibration data. Also provided is means for conditioning the test electrode so that the results will be reproducible, and means to provide an offset voltage. The probe may be provided with internal temperature sensing means such as a thermocouple in order to measure the pot temperature and to allow for compensation for temperature dependence of the anode effect. However temperature has a relatively small effect.

Figure 3:
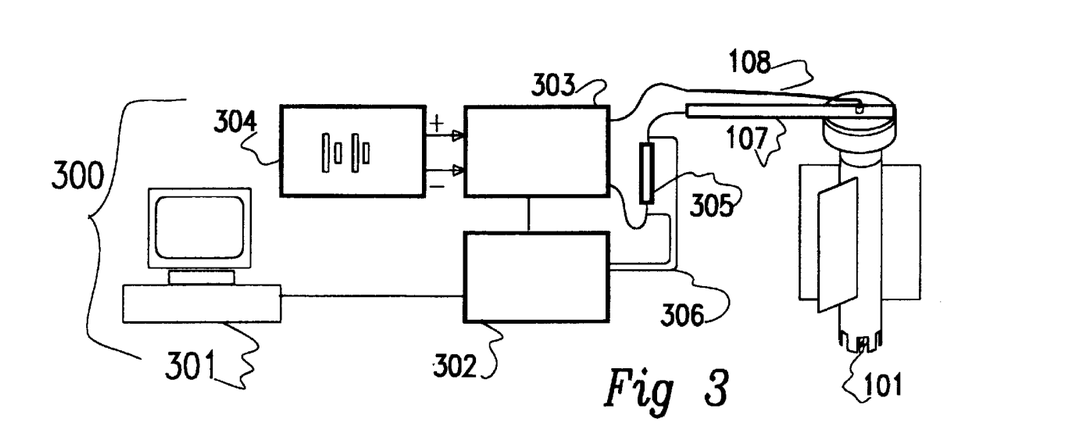
FIG. 3. Block diagram of control units.

FIG. 3 is a block diagram 300, showing electrical connections between a typical personal computer 301 (or some other processor, which may be tailored to perform just the specific function and be packaged so as operate reliably in the smelter environment which is generally quite hostile to electronic devices) and the electrode assembly at the right, where the support arm 107 and the wire 108 are connected to the amplifier 303. This acts as a variable, controllable voltage source at some substantial power level (such as 0–10 volts, 0–20 Amperes rating) and itself is preferably fed with a DC supply voltage from a lead-acid accumulator 304. Because of the power levels in a working smelter pot, the test electronics should all be electrically floating. The voltage gradient within the electrolyte is not significant and so measurements can be carried out without interrupting the power. Item 305 is a 0.01 ohm resistance, used as a current-to-voltage converter. Box 302 contains conventional analogue-to-digital (A-D) and digital-to-analogue (D-A) converters and conveniently may be a PCMCIA card within a personal computer. An A-D function periodically samples the electrode assembly current, meanwhile the D-A converter "instructs" the amplifier to supply a controlled voltage to the electrode assembly. Other process parameters may also be read automatically or be input through the keyboard. The personal computer may then calculate or derive and present the actual concentration of alumina on a screen. In the preferred embodiment of the invention the control system 300 will be powered by lead acid storage batteries 304 and consist of a portable (notebook or laptop) computer such an IBM 486 PC (301) with a PCMCIA digital to analogue and analogue to digital card such as a National Instruments Dac Card 1200 (302). This card is capable of sending a signal to an amplifier consisting usually of a transistor boost circuit. The voltage output (in 108) is connected to a graphite anode and an "Inconel" cathode which is from time to time inserted in a cryolite containing bath in an aluminium reduction cell. This device would presumably be portable, and be used in a given pot from time to time as a check on its operation. Alternatively a number of these units may be used in a pot line and the outputs networked to a central computer either by a hard wired connect or a remote signal connection (for example a radio signal connection).

Method

Figure 4:
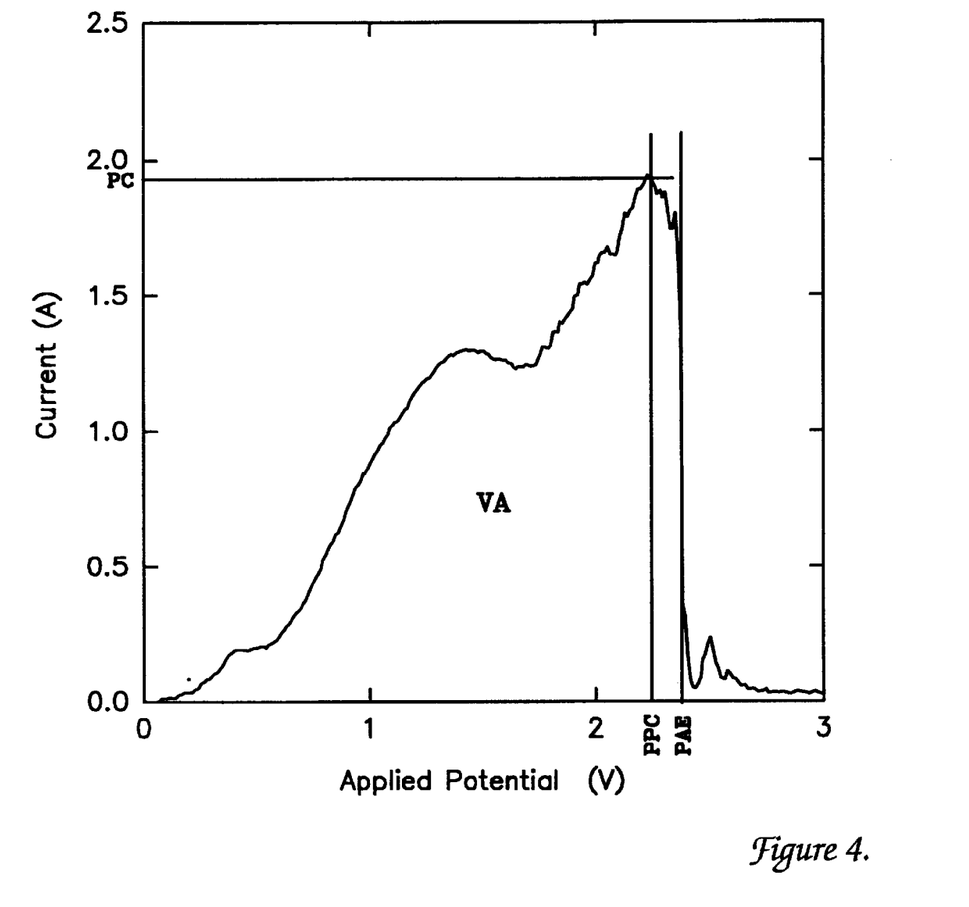
FIG. 4. Voltammogramme—showing determination of PAE (potential at which the anode effect occurs), VA (Voltage at which anode effect occurs), PPC (potential at which peak current occurs), and PC ( magnitude of peak current).
Figure 5:
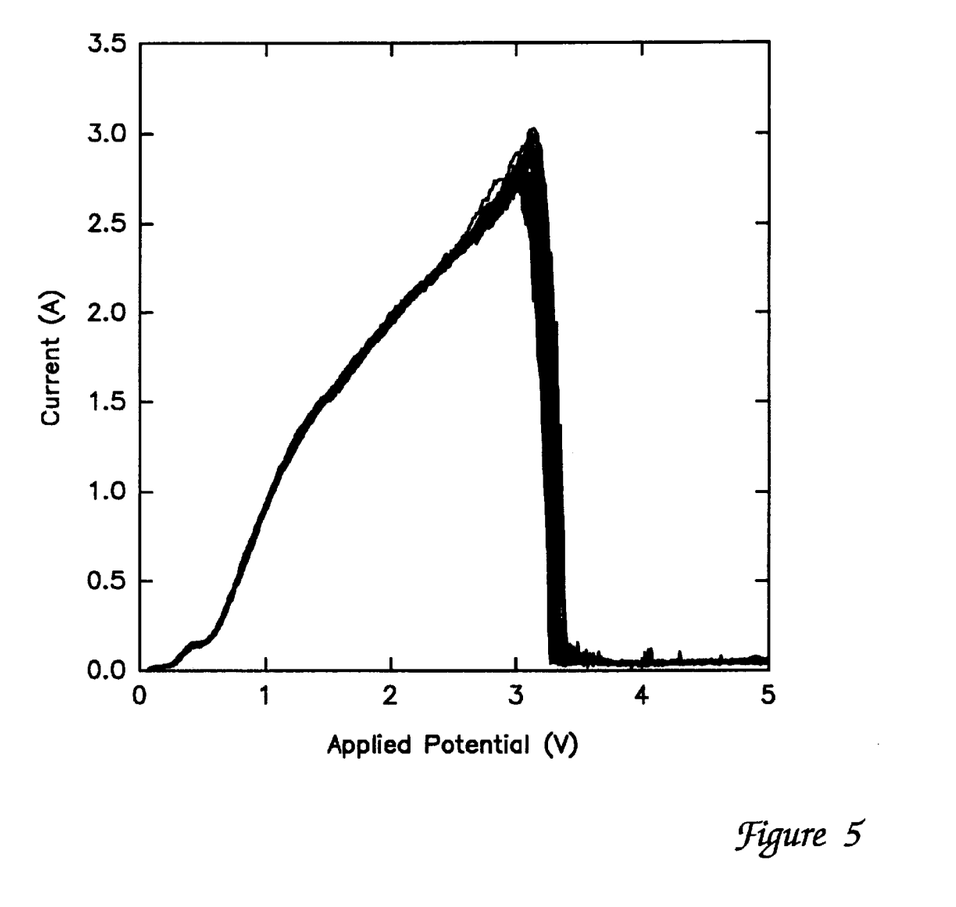
FIG. 5. Reproducibility of the anode effect.
Figure 6:
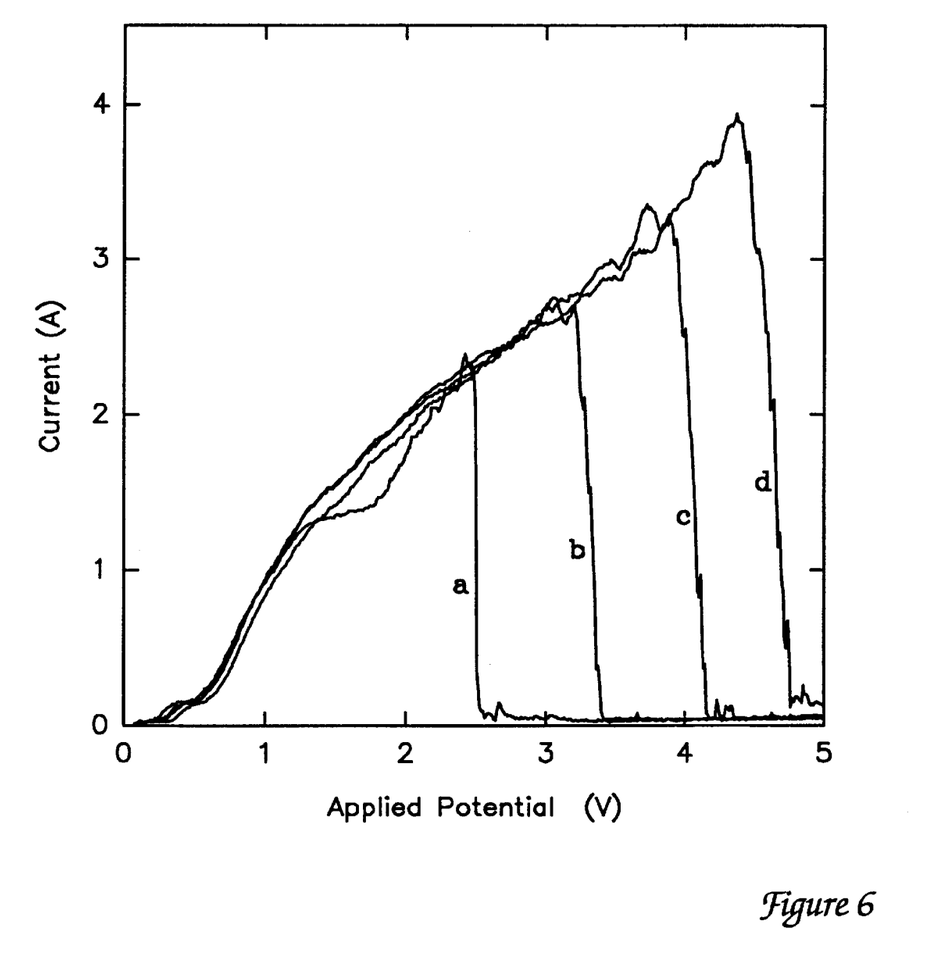
FIG. 6. Voltammogramme showing variation as a function of alumina concentration.

The "anode effect" is the effect wherein as the voltage across the cell is increased beyond a certain point the resistance of the cell rises and hence the current passing through the cell ceases to rise and begins to drop. It is shown in FIGS. 4, 5, and 6. The method can be regarded as a matter of assessing the alumina concentration within the cell by measuring the point at which the anode effect commences. Cyclic repetition and statistical processing, while minimising the time at or above the anode effect assist in increasing the accuracy of the estimation of alumina concentration.

The process is characterised by the following steps:

(a) A working electrode and a counter electrode are placed in a molten halogen containing bath.

(b) A potential difference is applied between the working electrode and the counter electrode so that the working electrode is anodic and the counter electrode is cathodic.

(c) When the probe of the measuring device is inserted in the molten halogen containing bath it is at ambient temperature and the electrolyte which is at a high temperature will freeze onto the probe. Measurements should not begin until the frozen material has remelted. To determine the point at which the frozen material has remelted a predetermined low voltage is applied between the working electrode and the counter electrode and the current is monitored. As the electrolyte melts this current will increase and in this way it is possible to determine when the remelting of the electrolyte is complete.

(d) The working electrode is then conditioned. This is done by carrying out a number of modified linear sweep voltammetry sweeps, typically between 1 and 100. This has the effect of giving stable and reproducible surface characteristics to the working electrode. The conditioning sweeps are typically the same as the analysis sweeps described in (f). An electrode which is being used for the first time may require more conditioning sweeps.

(e) The potential difference applied between the working electrode and the counter electrode is adjusted to maintain a constant low current in order to continue to maintain the working electrode anodic and the counter electrode cathodic.

(f) A number, typically between 1 and 100, of modified linear sweep voltammetry cycles are performed. These are predetermined and controlled voltammogrammes. These voltammogrammes consist of increasing the potential from the potential maintained in (e) at a constant rate, typically between 5 V.s−1 and 100 V.s−1, to a potential which is more than sufficient to produce an anode effect, typically up to 6 to 10 V, then decreasing the potential at a constant rate, typically between 50 V.s−1 and 1000 V.s−1 back to the rest potential of (e).

(g) The proportion of oxide ions in the electrolyte is calculated by first determining one of the following (or a combination of these methods): (i) the potential at which the anode effect occurs (PAE) ; (ii) the potential at which the peak current is observed (PPC); (iii) the magnitude of the peak current (PC); or (iv) the voltammogramme area ie. the amount of charge that is passed; assuming constant rates for sweeping.

(h) The proportion of oxide ions is calculated by taking the value obtained in (g), averaging it if more than one sweep was performed, then calculating the proportion of oxide ions from a calibration curve, or from an equation fitted to a calibration curve.

In any one cyclic sweep, the voltage is brought up from its offset or bias of about 0.3 V, keeping the graphite anode slightly positive, at a preferred rate of about 30 V.s−1, and the voltage and current are monitored by the analogue signal sampling device or A-D converter. Typically about 600 samples are taken during one sweep. In order to define the value of the anode effect, the software monitors the rise of current and keeps a record of the highest value recorded so far. After the current starts to fall (and while the voltage is still being increased) the instantaneous current value is repeatedly compared to the stored highest value (PPC) and when it has fallen to 50% of the stored highest value, the corresponding voltage (PAR) is taken as the anode effect voltage. The sweep may be terminated at that point and the applied voltage is brought back more quickly (for example at 300 V.s−1 to the offset value. There is then a preferred rest period which allows for events such as mixing or diffusion in the electrolyte adjacent to the anode. A preferred rest period is about 0.25 to 10 sec; typically we use 0.75 sec. A further voltammetry cycle may then be applied.

While a linear sweep is normally used in voltammetry, it may be possible or even preferable to use other waveforms, such as a portion of a sine wave (that from 0 to 90 degrees; amplitude perhaps 10–20% greater than the expected anode effect voltage) which would serve to approach the current density of interest relatively quickly and then traverse the expected area of the anode effect more slowly. This would increase the speed of measurement and/or allow more measurements to be taken off one electrode. The fast sweep rates preferred in this invention reduce problems associated with gas evolution, and reduce the oxidation rate of the electrode (anode).

Results

The voltammogrammes and calibration curves included in this specification were produced under the following laboratory conditions:

An amount of bath of the order of 600 g composed of 86.25% synthetic cryolite ($Na_3AlF_6$), 8% aluminium fluoride ($AlF_3$), 5% calcium fluoride ($CaF_2$) 0.75% alumina ($Al_2O_3$) was prepared. The bath was previously dried in a drying oven at 200° C. and then placed in a crucible which was heated in an oven to 960° C. in a nitrogen atmosphere. When the electrolyte had melted a graphite stirrer was inserted and the electrolyte stirred continuously.

The anode and the cathode of the probe were connected to the output of the amplifier in series with a 0.01Ω resistor. The output of the data acquisition card drives the amplifier while the input to the data acquisition card is taken from across the 0.01Ω resistor. The probe, which consists of a graphite anode (Union Carbide grade CMG) of 3.1 mm diameter, and sharpened at the tip, concentric with an "Inconel" cathode of 25 mm diameter is then dipped into the bath.

A potential difference of 0.5 V is applied between the anode and cathode and the current is monitored until a reading that is stable and over 0.1 A is obtained. (During this period the electrolyte in contact with the assembly will have frozen, and melted again.) The potential is then adjusted until a current reading of 50 mA is obtained. This is the anodic offset potential which is maintained throughout in order to prevent the anode from ever becoming cathodic. Other potentials referred to in the following are potentials above this offset potential.

A potential is then applied to the anode starting from zero volts above the anode offset potential and rising at a rate of 20 V.s−1 to a potential of 6 V then decreasing back to zero volts at a rate of 200 V.s−1. This is referred to as a sweep. A period of 0.5 s then elapses before the increasing potential is applied again. This is repeated 20 times. The conditioning stage is now complete.

The measurement is carried out by carrying out another 20 sweeps. The proportion of oxide ions in the electrolyte is then calculated by first determining one of the following (or a combination of these methods): (i) the potential at which the anode effect occurs (FIG. 4-PAE), (ii) the potential at which the peak current is observed (FIG. 4-PPC), (iii) the magnitude of the peak current (FIG. 4-PC) (iv) the voltammogramme area (FIG. 4-VA) ie. the amount of charge that is passed. For example the potential at the anode effect may be found for each sweep by determining the point at which the current first drops below ⅔ of its maximum value. These 20 determinations of the anode effect are then averaged and this gives the value of the potential at the anode effect for 0.75% alumina in the electrolyte composition used. An example of the reproducibility of the voltammogrammes is shown in FIG. 5, which comprises a repeated trace of 20 superimposed voltammogrammes for 0.75% alumina.

A charge of preweighed alumina of an amount 1% of the mass of the combined bath and alumina mass is added to the bath and the mixture stirred for sufficient time for all the alumina to dissolve. The conditioning and measurement procedure is carried out once again to obtain a value of the potential at the anode effect for 1.75% alumina in the electrolyte. This is repeated to build up a calibration curve for potential of the anode effect versus alumina concentration as for example in FIG. 7. The shape of the voltammogramme changes with increasing alumina concentration as can be seen in FIG. 6, where:

a=0.75% alumina, b=1.75% alumina, c=2.75% alumina, and d=4.5% alumina.

Figure 7:
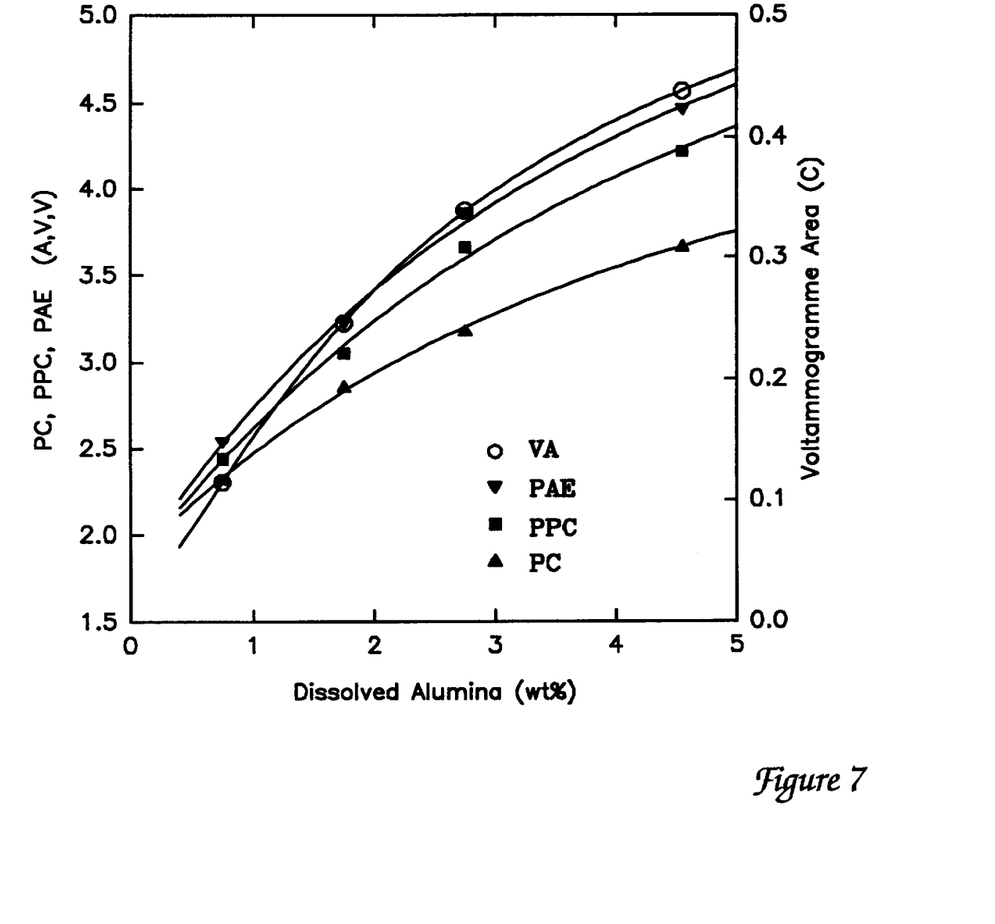
FIG. 7. Example of a calibration curve.

FIG. 7 illustrates the various measurements that may be taken from individual curves, plotted against concentration of alumina. Evidently, all parameters are proportional to alumina content, though some may be less sensitive to variations of the concentration of other components within a bath.

Once calibration on a laboratory scale is complete the invention may be used in industrial cells by following the same procedure as above except that the probe is inserted directly into a reduction cell and no stirring is necessary.

ADVANTAGES

The present invention works very well at low levels of alumina and at the range of concentrations used in industrial aluminium reduction cells. It has much better reproducibility and reliability than other methods disclosed in the patent literature.

This process has the advantage over chronopotentiometry (or chronoamperometry) in that the maximum voltage applied to the electrode is much less so that the electrode suffers much less wear and consequently has a longer and more reliable life. The results are also more reproducible and accurate than those of chronopotentiometry.

Other features of this method include the absence of the need for a reference electrode as would normally be used in voltammetry.

VARIATIONS

The method is also applicable to the detection of metals of the rare earth group including neodymium, cerium lanthanum and yttrium.

We claim:

1. A method for measuring the concentration of alumina in a molten electrolyte in a bath, employing characteristic anode effect produced by an electrode assembly means having a cathode and an anode and which assembly means is placed in the bath, wherein at least one rapid cyclic voltammetry sweep is applied to the electrode assembly means by means of a voltage-controlled source of electric power connected to the electrode assembly, and the current passing through the electrode assembly means is monitored during the at least one sweep in order to detect the anode effect, and the voltage at which the anode effect is observed is recorded, in order to derive information capable of providing a measurement.

2. A method as claimed in claim 1, wherein the at least one sweep comprises a substantially linear change in voltage and is applied to the anode of the electrode assembly means at a rate of voltage change of between +5 to +100 volts per second during a first measurement phase, yto reach a potential which is more than sufficient to produce the anode effect, and then is returned at a rate of between −50 to −1000 volts per second during a second, return phase prior to a rest phase.

3. A method as claimed in claim 2, wherein the constant rate of voltage change during the first measurement phase is between +20 V.s−1 and +50 V.s−1, and the constant rate of voltage change during the second return phase is between −100 V.s−1 and −300 V.s−1.

4. A method for measuring the concentration of alumina in a smelting pot as claimed in claim 3, wherein the electrode assembly includes a working electrode and a counter electrode, and a small offset potential difference of less than about one volt is applied between the working electrode and the counter electrode so that the working electrode is maintained in an anodic state and the counter electrode is maintained in a cathodic state between voltammetry sweeps.

5. A method for measuring the concentration of alumina in a smelting pot as claimed in claim 4 wherein prior to measurement the working electrode is conditioned by carrying out between 1 and 200 cyclic linear voltammetry sweeps.

6. A method for measuring the concentration of alumina in a smelting pot as claimed in claim 4, wherein when if a portion of the electrolyte solidifies about the electrodes forming frozen material, after placement and prior to measurement, a predetermined low voltage is applied between the working electrode and the counter electrode and the current flow resulting from the voltage is monitored in order to detect an increase of current indicating that the frozen material has been melted.

7. A method for measuring the concentration of alumina in a smelting pot as claimed in claim 4, wherein the molten electrolyte includes a proportion of oxide ions and said proportion of oxide ions is calculated using at least some of the following information: the potential at which the anode effect occurs, the potential at which the peak current is observed, the magnitude of the peak current, the area of the entire voltammogramme; and then calculating the proportion of oxide ions with reference to a calibration curve.

8. A method for measuring the concentration of alumina in a smelting pot as claimed in claim 4, wherein the molten electrolyte includes a proportion of oxide ions and said proportion of oxide ions is calculated using at least some of the following information: the potential at which the peak current has reverted to about half its peak value; and then calculating the proportion of oxide ions with reference to a calibration curve.

9. Apparatus suitable for measuring the concentration of alumina in a smelting pot, the apparatus including an electrode assembly capable of being inserted into the molten electrolyte and having electrical connections to a voltage-controlled power supply and to voltage and current measurement means, wherein the electrode assembly means includes an exposed carbon anode having an elongated shape with a length to width ratio of more than about 2.0, and a cathode.

10. Apparatus suitable for measuring the concentration of alumina in a smelting pot, comprising:

an electrode assembly capable of being inserted into the molten electrolyte and having electrical connections to a voltage-controlled power supply and to voltage and current measurement means, wherein the electrode assembly means includes an exposed carbon anode having an elongated shape with a length to width ratio of more than about 2.0. and a cathode;

automated means capable of applying a varying yet controlled voltage across the electrode assembly, the means being capable of causing the controlled voltage to rise from a first value to a second value at a first controlled rate and then to return from the second value to the first value at a second controlled rate;

means capable of recording, at any applied voltage, the current passing between the anode and the cathode; and means capable of extracting at least the anode effect voltage from the recorded current information.

11. Apparatus suitable for measuring the concentration of alumina in a smelting pot as claimed in claim 9, wherein the carbon anode comprises a cylindrical member having sidewall portions exposed to the electrolyte.

* * * * *